(12) United States Patent
Challita

(10) Patent No.: US 12,402,156 B2
(45) Date of Patent: Aug. 26, 2025

(54) SCHEDULING RADIO RESOURCES IN A COMMUNICATIONS NETWORK

(71) Applicant: Telefonaktiebolaget LM Ericsson (publ), Stockholm (SE)

(72) Inventor: Ursula Challita, Solna (SE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 404 days.

(21) Appl. No.: 17/926,600

(22) PCT Filed: May 28, 2020

(86) PCT No.: PCT/SE2020/050542
§ 371 (c)(1),
(2) Date: Nov. 20, 2022

(87) PCT Pub. No.: WO2021/242152
PCT Pub. Date: Dec. 2, 2021

(65) Prior Publication Data
US 2023/0199822 A1    Jun. 22, 2023

(51) Int. Cl.
*H04W 72/542* (2023.01)
*A61B 5/00* (2006.01)
(Continued)

(52) U.S. Cl.
CPC ......... *H04W 72/542* (2023.01); *A61B 5/0022* (2013.01); *A61B 5/021* (2013.01);
(Continued)

(58) Field of Classification Search
CPC . H04W 72/542; H04W 52/023; H04W 16/22; A61B 5/0022; A61B 5/021;
(Continued)

(56) References Cited

U.S. PATENT DOCUMENTS

2007/0276439 A1  11/2007  Miesel et al.
2009/0105560 A1   4/2009  Solomon
(Continued)

FOREIGN PATENT DOCUMENTS

| CN | 111465032 A | * | 7/2020 | ............ H04W 16/22 |
| CN | 111586614 A | * | 8/2020 | ............ H02J 50/001 |

(Continued)

OTHER PUBLICATIONS

Search Report, European Patent Application No. 20937680.5, mailed Jan. 25, 2024, 9 pages.
(Continued)

*Primary Examiner* — Vinncelas Louis
(74) *Attorney, Agent, or Firm* — Sage Patent Group

(57) ABSTRACT

A computer implemented method in a node of a communications network for scheduling radio resources to a user equipment, UE, in order to provide a service to a user of the UE. The method includes obtaining one or more physiological parameters of the user of the UE. The method further includes scheduling resources to the UE, based on the one or more physiological parameters, so as to provide the service to the UE with a predetermined quality of experience, as perceived by the user.

20 Claims, 3 Drawing Sheets

(51) Int. Cl.
  *A61B 5/021* (2006.01)
  *A61B 5/024* (2006.01)
  *A61B 5/16* (2006.01)
  *G06N 3/045* (2023.01)
  *G06N 3/09* (2023.01)
  *H02J 50/00* (2016.01)

(52) U.S. Cl.
  CPC .............. *A61B 5/024* (2013.01); *A61B 5/165* (2013.01); *G06N 3/045* (2023.01); *G06N 3/09* (2023.01); *H02J 50/001* (2020.01)

(58) Field of Classification Search
  CPC ..... A61B 5/1118; A61B 5/165; A61B 5/7267; A61B 5/024; G06N 3/045; G06N 3/09; H02J 50/001
  See application file for complete search history.

(56) References Cited

U.S. PATENT DOCUMENTS

| | | | |
|---|---|---|---|
| 2012/0119902 A1* | 5/2012 | Patro ................. | H04W 52/0238 340/502 |
| 2014/0095181 A1 | 4/2014 | Johnson et al. | |
| 2014/0269526 A1 | 9/2014 | Mitola, III | |
| 2016/0081097 A1 | 3/2016 | Cho | |
| 2018/0242920 A1 | 8/2018 | Hresko et al. | |

FOREIGN PATENT DOCUMENTS

| | | |
|---|---|---|
| EP | 2278508 A1 | 1/2011 |
| WO | 2017105300 A1 | 6/2017 |
| WO | WO 2018/018823 A1 | 2/2018 |
| WO | WO 2021/025601 A1 | 2/2021 |

OTHER PUBLICATIONS

Koutsakis Polychronis Ed—Konstantopoulos Charalampos et al: "Scheduling for telemedicine traffic transmission over WLANs", Computer Communications, Elsevier Science Publishers BV, Amsterdam, NL, vol. 108, Apr. 29, 2017 (Apr. 29, 2017), pp. 17-26.
International Search Report and Written Opinion of the International Searching Authority, PCT/SE2020/050542, mailed Apr. 26, 2021, 11 pages.
Yang, G., et al., "Application of Improved Particle Algorithm in Wireless Network Power Energy Efficiency," 2019 International Conference on Computer Network, Electronic and Automation (ICCNEA), Sep. 27, 2019 (XP033667439).
Mirkovic, M., et al., "Evaluating the Role of Content in Subjective Video Quality Assessment," Hindawi Publishing Corporation, The Scientific World Journal, vol. 2014, Article ID 625219, 9 pages.
Motyka, P., et al., "Interactions between cardiac activity and conscious somatosensory perception," Psychophysiology. 2019; 56:e13424. https://doi.org/10.1111/psyp.13424, 31 pages.
Kasgari, A. T. Z., et al., "Human-in-the-Loop Wireless Communications: Machine Learning and Brain-Aware Resource Management," in IEEE Transactions on Communications, vol. 67, No. 11, Nov. 2019, 31 pages.
Yang, Y., et al., "Prospect Pricing in Cognitive Radio Networks," IEEE Transactions on Cognitive Communications and Networking, vol. 1, No. 1, Mar. 2015, 14 pages.
Tao, X., et al., "Real-Time Personalized Content Catering via Viewer Sentiment Feedback: A QoE Perspective," IEEE Network, Nov./Dec. 2015, 6 pages.
Mannucci, T., "Safe Exploration Algorithms for Reinforcement Learning Controllers," IEEE Transactions on Neural Networks and Learning Systems, vol. 29, No. 4, Apr. 2018, 13 pages.

* cited by examiner

SCHEDULING RADIO RESOURCES IN A COMMUNICATIONS NETWORK

CROSS REFERENCE TO RELATED APPLICATIONS

This application is a 35 U.S.C. § 371 national stage application of PCT International Application No. PCT/SE2020/050542 filed on May 28, 2020, the disclosure and content of which is incorporated by reference herein in its entirety.

TECHNICAL FIELD

This disclosure relates to methods, nodes and systems in a communications network. More particularly but non-exclusively, the disclosure relates to scheduling resources in a communications network.

BACKGROUND

User-centric applications such as virtual reality and immersive gaming will be increasingly widespread applications in future wireless networks. Common features of such services include: a) a high level of interaction between the user and application, and b) their need for more network resources compared to conventional cellular applications. It represents a challenge to network resources to provide resources to such intensive applications. It is an object of embodiments herein to improve on the provision of resources in a communications network, particularly to resource intensive applications that involve a high degree of user interaction.

SUMMARY

As described above, new user-centric applications such as virtual reality and immersive gaming will put increasing pressures on communications networks. Existing radio resource algorithms allocate radio resources based on the channel and network conditions. For example, Base Stations (BS) may seek to allocate Resource Blocks (RBs) and power to users according to the delay needs and channel state of the BS, while ignoring the user's behavior and state. Conventional algorithms are still reliant on device-level features and are agnostic to the human end-users and their features (e.g., brain limitation or behavior). Hence, conventional algorithms may waste network resources by allocating more resources to a human user who cannot perceive the associated QoS gains, e.g. due to cognitive brain limitations. Thus improvements to resource scheduling may be made when deploying user-centric applications over wireless and cellular systems by making the network aware not only of the quality-of-service (QoS) needs of the applications, but also of the perceptions of the human users of this QoS (see paper by A. Kasgari, W. Saad, and M. Debbah, entitled "Human-in-the-Loop Wireless Communications: Machine Learning and Brain-Aware Resource Management").

In a paper by Y. YANG, L. Park, N. Mandayam, I. Seskar, A. Glass, and N. Sinha, entitled "Prospect Pricing in Cognitive Radio Networks", the authors run an experiment by comparing the subjective and objective measurements of the quality of a video. For each pair of packet loss and delay chosen, they objectively measure (using decoded video frames per second) the corresponding decoded frames per second at the video player used to display the video. The psychophysics experiments have revealed that the decoded video frames per second serves as the best objective proxy for the quality of the video among the parameters chosen, while the feelings about the number of stops and stutters occurred is the best proxy for the subjective ratings on the overall video quality. The human subjects were also asked to subjectively evaluate on a four level scale the quality of the video as they perceive it, with 4 being the highest rating and 1 being the lowest rating. Results showed that the relationship between the objective and subjective probabilities displayed an inverse S-shaped probability weighting effect.

In embodiments herein, an AI-assisted brain-aware resource management process is proposed, wherein the proposed resource allocation methodology takes into account the human behavior and mental state, alongside the channel state information.

In a first aspect there is a computer implemented method in a node of a communications network for scheduling radio resources to a user equipment, UE, in order to provide a service to a user of the UE. The method comprises obtaining one or more physiological parameters of the user of the UE, and scheduling resources to the UE, based on the one or more physiological parameters, so as to provide the service to the UE with a predetermined quality of experience, as perceived by the user.

Physical parameters may be correlated with alertness of the user. Thus, by taking physiological parameters of the user into account when scheduling resources in a communications network, resources may be allocated in a manner that takes the human behavior and mental state into account, e.g. alongside network parameters such as channel state information. Such information may be obtained and used in a transparent manner, e.g. by alerting the user to the use of the physiological parameters or asking the user for permission to use such information. Thus the user may be made aware of the effects of using the disclosed method, as well as how the method actually works.

According to a second aspect there is a node in a communications network for scheduling radio resources to a user equipment, UE, in order to provide a service to a user of the UE. The node comprises a memory comprising instruction data representing a set of instructions, and a processor configured to communicate with the memory and to execute the set of instructions. The set of instructions, when executed by the processor, cause the processor to obtain one or more physiological parameters of the user of the UE, and schedule resources to the UE, based on the one or more physiological parameters, so as to provide the service to the UE with a predetermined quality of experience, as perceived by the user.

According to a third aspect there is a computer program product comprising a computer readable medium, the computer readable medium having computer readable code embodied therein, the computer readable code being configured such that, on execution by a suitable computer or processor, the computer or processor is caused to perform the method of the first aspect.

BRIEF DESCRIPTION OF THE DRAWINGS

For a better understanding and to show more clearly how embodiments herein may be carried into effect, reference will now be made, by way of example only, to the accompanying drawings, in which.

DETAILED DESCRIPTION

Under certain scenarios, the human brain may not be able to perceive any difference between videos transmitted with different QoS (e.g., rates or delays). To deliver immersive, human-centric services, the network must tailor the usage and optimization of wireless resources to the intrinsic features of its human users such as their behavior and brain processing limitations thus utilizing the available radio resources more efficiently.

As noted above, embodiments herein relate to scheduling resources in a communications network based on physiological parameters of an end-user. For example, physiological parameters may be used as a proxy for attentiveness and perception of the brain. In this way, for example, more resources may be allocated if a user is alert and has high cognitive processing compared to if the user has low cognitive processing and thus will not perceive increased QoS associated with any additional resources.

Embodiments herein relate to a communications network. Generally, the communications network (or telecommunications network) may comprise any one, or any combination of: a wired link (e.g. ASDL) or a wireless link such as Global System for Mobile Communications (GSM), Wideband Code Division Multiple Access (WCDMA), Long Term Evolution (LTE), WiFi, or Bluetooth wireless technologies. The skilled person will appreciate that these are merely examples and that the communications network may comprise other types of links. A wireless network may be configured to operate according to specific standards or other types of predefined rules or procedures. Thus, particular embodiments of the wireless network may implement communication standards, such as Global System for Mobile Communications (GSM), Universal Mobile Telecommunications System (UMTS), Long Term Evolution (LTE), and/or other suitable 2G, 3G, 4G, or 5G standards; wireless local area network (WLAN) standards, such as the IEEE 802.11 standards; and/or any other appropriate wireless communication standard, such as the Worldwide Interoperability for Microwave Access (WiMax), Bluetooth, Z-Wave and/or ZigBee standards.

Figure 1:
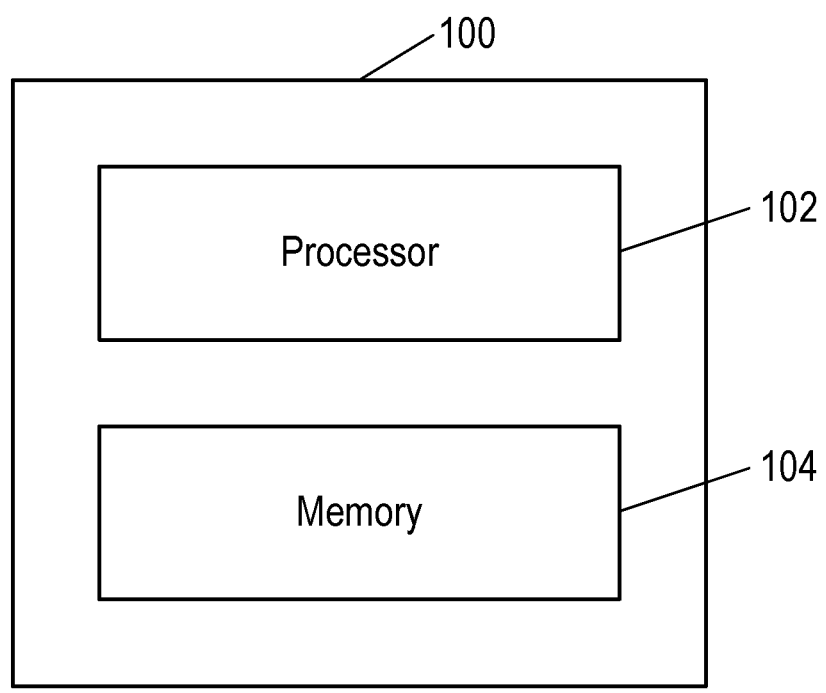
FIG. 1 illustrates a node in a communications network according to some embodiments.

FIG. 1 illustrates a node in a communications network according to some embodiments herein. Generally, the node 100 may comprise any component or network function (e.g. any hardware or software module) in the communications network suitable for performing the functions described herein.

For example, in some embodiments, a node may comprise equipment capable, configured, arranged and/or operable to communicate directly or indirectly with a UE (such as a wireless device) and/or with other network nodes or equipment in the communications network to enable and/or provide wireless or wired access to the UE and/or to perform other functions (e.g., administration) in the communications network. Examples of nodes include, but are not limited to, access points (APs) (e.g., radio access points), base stations (BSs) (e.g., radio base stations, Node Bs, evolved Node Bs (eNBs or eNodeB) and NR NodeBs (gNBs or GNodeBs)). Further examples of nodes include, but are not limited to, core network functions such as, for example, core network functions in a Fifth Generation Core network (5GC), such as the Access and Mobility Management function (AMF), Session Management function (SMF) and Network Slice Selection Function (NSSF).

The node 100 may be configured or operative to perform the methods and functions described herein, such as the methods 200 or 300 as described below. The node 100 may comprise a processor (e.g. processing circuitry or logic) 102. It will be appreciated that the node 100 may comprise one or more virtual machines running different software and/or processes. The node 100 may therefore comprise one or more servers, switches and/or storage devices and/or may comprise cloud computing infrastructure or infrastructure configured to perform in a distributed manner, that runs the software and/or processes.

The processor 102 may control the operation of the node 100 in the manner described herein. The processor 102 can comprise one or more processors, processing units, multi-core processors or modules that are configured or programmed to control the node 100 in the manner described herein. In particular implementations, the processor 102 can comprise a plurality of software and/or hardware modules that are each configured to perform, or are for performing, individual or multiple steps of the functionality of the node 100 as described herein.

The node 100 may comprise a memory 104. In some embodiments, the memory 104 of the node 100 can be configured to store program code or instructions that can be executed by the processor 102 of the node 100 to perform the functionality described herein. Alternatively or in addition, the memory 104 of the node 100, can be configured to store any requests, resources, information, data, signals, or similar that are described herein. The processor 102 of the node 100 may be configured to control the memory 104 of the node 100 to store any requests, resources, information, data, signals, or similar that are described herein.

It will be appreciated that the node 100 may comprise other components in addition or alternatively to those indicated in FIG. 1. For example, in some embodiments, the node 100 may comprise a communications interface. The communications interface may be for use in communicating with other nodes in the communications network, (e.g. such as other physical or virtual nodes). For example, the communications interface may be configured to transmit to and/or receive from other nodes or network functions requests, resources, information, data, signals, or similar. The processor 102 of node 100 may be configured to control such a communications interface to transmit to and/or receive from other nodes or network functions requests, resources, information, data, signals, or similar.

The node 100 is for scheduling radio resources to a user equipment, UE, in order to provide a service to a user of the UE. Briefly, in one embodiment, the node 100 may be configured to obtain one or more physiological parameters of the user of the UE, and schedule resources to the UE, based on the one or more physiological parameters, so as to provide the service to the UE with a predetermined quality of experience, as perceived by the user.

Figure 2:
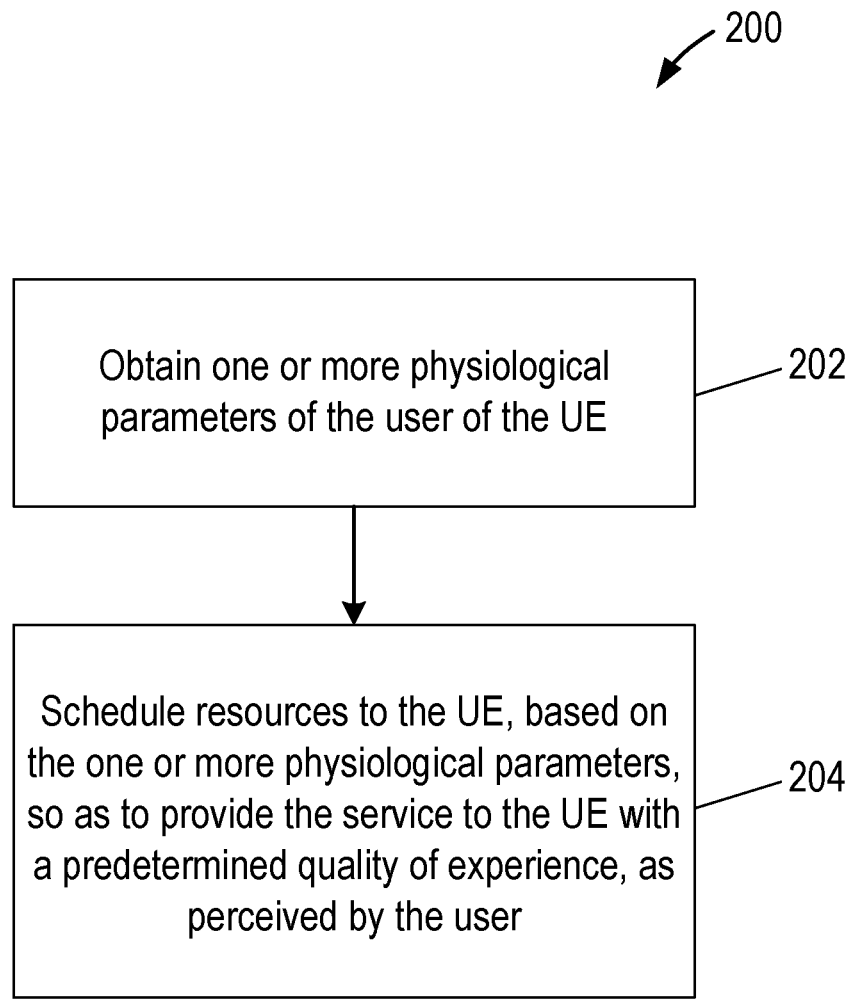
FIG. 2 illustrates a method in a node of a communications network according to some embodiments.

FIG. 2 illustrates a method 200 in a node of scheduling radio to a user equipment, UE, in order to provide a service to a user of the UE according to some embodiments herein. In a first step the method 200 comprises obtaining 202 one or more physiological parameters of the user of the UE. In a second step the method comprises scheduling 204 resources to the UE, based on the one or more physiological parameters, so as to provide the service to the UE with a predetermined quality of experience, as perceived by the user.

Brain-aware radio resource management schemes as described herein can result in enhanced radio resource utilization. For example, as described in more detail below, in some embodiments, more resource blocks and/or higher transmission power may be allocated to users with a high delay perception threshold compared to users with a low delay perception threshold, while accounting for the delay requirement of the underlying application. Users with high delay perception threshold can correspond to users at old ages, users during performing activity, or users in a tired mental state. This may result in i) lower costs and higher revenues for operators, ii) power savings in the network while preserving the perceived QoS of the users iii) minimised waste of radio resources and provision of the service to the user more precisely based on their real brain processing capability, iv) energy efficiency.

Turning back to FIG. 2, in more detail, the method 200 may be performed by the node 100 as described above. In some embodiments, steps 202 and 204 of the method may be performed by first and second processing modules of the processor 102 of the node 100.

The node may schedule radio resources for a user equipment in order to provide a service to the user equipment. In more detail, the UE may comprise a device capable, configured, arranged and/or operable to communicate wirelessly with network nodes and/or other wireless devices. Unless otherwise noted, the term UE may be used interchangeably herein with wireless device (WD). Communicating wirelessly may involve transmitting and/or receiving wireless signals using electromagnetic waves, radio waves, infrared waves, and/or other types of signals suitable for conveying information through air. Examples of a UE include, but are not limited to, a smart phone, a mobile phone, a cell phone, a voice over IP (VoIP) phone, a wireless local loop phone, a desktop computer, a personal digital assistant (PDA), a wireless camera, a gaming console or device, a virtual reality device or virtual reality console, a music storage device, a playback appliance, a wearable terminal device, a wireless endpoint, a mobile station, a tablet, a laptop, a laptop-embedded equipment (LEE), a laptop-mounted equipment (LME), a smart device, a wireless customer-premise equipment (CPE), a personal wearable device (e.g., watches, fitness trackers, etc.).

A service may comprise any application that runs on the user equipment. In some embodiments, the service may require (e.g. real-time) interaction with a user. For example, the service may comprise a gaming application, a virtual reality application or any other user-centric application. In other embodiments, the service may comprise a video-streaming application, a music-streaming application, or any other application where audio or visual content is transmitted to the user.

The node 100 may schedule resources to the UE. The node 100 may provide the scheduled resources to the UE (e.g. the node may schedule its own resources) or the node may schedule the resources of another node in order for the other node to provide the service to the UE.

In a step 202, the method 200 may comprise obtaining one or more physiological parameters of the user of the UE. E.g. the user of the UE that has requested the service. Physiological parameters in this sense may comprise parameters such as, for example, any one or more of the following: a heart rate, a blood pressure, a measure of stress being experienced by the user and/or a measure of an activity level of the user. An activity level may be determined, for example, based on a determined type of activity (e.g. walking, dancing, static, running, biking etc). A physiological parameter may also comprise a measure of fatigue of the user. The skilled person will appreciate that these are merely examples however and that other physiological parameters may also be obtained in step 202.

Generally, the step of obtaining 202 one or more physiological parameters of the user of the UE may comprise obtaining the one or more physiological parameters from one or more sensors on the UE. The UE may thus comprise one or more sensors that may be used to measure the physiological parameter(s), for example, the UE may comprise any one or more of a sensor for measuring a heart-rate, a sensor for measuring blood pressure, a pulse oximeter (SpO2) sensor, a skin conductivity sensor, or any other sensor for measuring a physiological parameter.

In some embodiments the UE or the node 100 may be configured to interact with another UE or device in order to obtain the physiological measurements. For example, the UE or node 100 may interact with a fitness tracker or smart watch of the user in order to obtain the physiological parameter(s).

Physiological parameters may be most closely related to (e.g. correlated with) the alertness of the user and thus their brain perception abilities at any given time. Thus, scheduling resources based on physiological parameters may provide an increasingly accurate method of gauging the perceptiveness of the human brain and scheduling resources accordingly.

In some embodiments the step of obtaining 202 may further comprise obtaining other human-centric parameters in addition to the physiological parameters described above. For example, the gender or age of the user, or the time of day at which the user wishes to access the service. In general any parameter may be further incorporated that may be correlated to a user's cognitive speed.

It is noted that the user may consent to this information being obtained or used in this way. In some embodiments, the user may e.g. provide additional information, such as age or gender, etc.

In step 204 the method comprises scheduling resources to the UE, based on the one or more physiological parameters, so as to provide the service to the UE with a predetermined quality of experience, as perceived by the user.

Resources in this sense may comprise, for example, the power and/or physical resource blocks (PRB) allocated to providing the service.

Generally, step 204 may comprise scheduling (e.g. providing the service using) more resources if the physiological parameters indicate that the user is alert or has a higher speed of perception than if the physiological parameters indicate that the user is fatigued or has a lower speed of perception.

In some embodiments, the predetermined quality of experience as perceived by the user is based on whether the user perceives (or is able to perceive) a delay in the service. In such embodiments, the step of scheduling resources 204 to the UE may comprise determining from the one or more physiological parameters a delay perception threshold at which a delay is perceptible to the user, and scheduling resources to the UE based on the delay perception.

In this context a delay perception threshold comprises an amount of delay that is noticable to the user. The more tired or fatigued the user is, the larger (or higher) their delay perception threshold will be. As such they will tolerate a higher delay, and the larger the margin for satisfying this delay is given to the network and therefore the larger the range of power allocation or PRB action selection the network can take so as to minimize energy consumption.

In some embodiments therefore, the step of scheduling resources to the UE based on the delay perception may comprise scheduling the resources so as to provide the service with a delay that is less than the delay perception threshold.

The delay perception threshold may be determined from the one or more physiological parameters in various ways, for example, using a look-up table, or mapping between the physiological parameters and the delay perception threshold. Such look-up tables or mappings may be determined experimentally.

In some embodiments, the delay perception threshold may be determined from the one or more physiological parameters by predicting the delay perception threshold using a first machine learning model that takes as input the one or more physiological parameters and outputs a prediction of the delay perception threshold of the user, based on the one or more physiological parameters.

The skilled person will be familiar with machine learning models (e.g. models trained using a machine learning process). But in brief, machine learning can be used to find a predictive function for a given dataset; the dataset is typically a mapping between a given input to an output. The predictive function (or mapping function) is generated in a training phase, which involves providing example inputs and corresponding ground truth (e.g. correct) outputs to the model. A test or validation phase then comprises predicting the output for a given, previously unseen, input. Applications of machine learning include, for example, curve fitting, facial recognition and spam filtering.

Herein, the first machine learning model may comprise a supervised learning model, such as, for example, a classification or regression model. For example, in some embodiments, the machine learning model may comprise a neural network model, a random forest model or a support vector regression model. Although these are provided as example machine learning models, it will be appreciated that the teachings herein apply more generally to any type of model that can be trained to take as input one or more physiological parameters and output a prediction of a delay perception threshold of the user.

As an example, the first machine learning model may comprise a (deep) neural network. The skilled person will be familiar with neural networks, but in brief, neural networks are a type of machine learning model that can be trained to predict a desired output for given input data. Neural networks are trained using training data comprising example input data and the corresponding "correct" or ground truth outcome that is desired. Neural networks comprise a plurality of layers of neurons, each neuron representing a mathematical operation that is applied to the input data. The output of each layer in the neural network is fed into the next layer to produce an output. For each piece of training data that is provided to the neural network, weights associated with the neurons are adjusted (e.g. using methods such as back-propagation and gradient descent) until the optimal weightings are found that produce predictions for the training examples that reflect the corresponding ground truths.

The first machine learning model may have been trained using training data comprising training examples wherein each training example comprised: a set of example values of the one or more physiological parameters for an example user and a ground truth delay perception threshold for the example user, at the time the example values of the one or more physiological parameters were obtained.

The delay perception threshold may have been determined for each user, for example, by asking the user to indicate whether they perceive a delay in the service when provided with different resource levels. In other words, the ground truth delay perception threshold may be based on feedback provided by the example user, of a quality of experience of an example service provided to the example user.

In some embodiments there is a method of training a supervised machine learning model to predict a delay perception threshold of a user based on one or more physiological parameters of the user. The method comprises providing training data to the machine learning model, the training data comprising training examples, each training example comprising: i) one or more physiological parameters of an example user and ii) a respective delay perception threshold of the example user.

A detailed embodiment where the delay perception threshold of the user is predicted using a first machine learning model is provided below.

Training data collection process: For training the first machine learning model, training data may be collected from multiple users, under different state and brain conditions, by asking the users to rate the quality of a video while the delay and packet loss in the system is increased. For quality rating, one could consider metrics such as video distortion level, delay, and bit rate.

As noted above, input features to the first machine learning model may comprise physiological parameters, including but not limited to:
  Heart rate
  level of activity: number of steps/sec
  stress level
  type of activity: walking, dancing, static, running, biking, . . .
  level of fatigue
Further human-centric parameters may also be provided as inputs, such as, for example:
  Gender
  Age
  time of the day
As described above, this data can be collected via various sensors such as those on the UE or an associated device (smart watch/fitness tracker) of the user. The users are requested to inform the network their level of satisfaction of the perceived signal quality.

Training procedure: as noted above, supervised machine learning techniques may be used to train the first machine learning model to learn a mapping between the above input features and the desired output of the model, which can be defined as the delay perception threshold of the brain. One can consider machine learning algorithms such as random forest and feed-forward neural networks. The loss function can be defined as the mean squared error of all the training examples. In this way, the delay perception threshold of the brain may be predicted using a first machine learning model, based on obtained physiological parameters of the user.

Turning back to FIG. 2, once the delay perception threshold of the user has been determined, the method 200 may comprise scheduling the resources so as to provide the service with a delay that is less than the delay perception threshold. In this way, sufficient resources can be scheduled to the user so that the user perceives a high quality of service (e.g. without any delay), but without over-provisioning resources to the user, the benefits of which will not be appreciated by the user due to their cognitive state.

Generally, the step of scheduling resources to the UE may comprise providing the service using fewer resources if the delay perception threshold of the user is higher compared to if the delay perception threshold of the user is lower. For example, the method may comprise providing the service using fewer resources by transmitting packets related to the service with lower power and/or allocating fewer resource blocks to the service. For instance, in scenarios where the delay perception threshold of the user is high (e.g., user is tired or in activity), the node 100 may transmit the service to the user with lower power, and/or allocating a smaller number of resource blocks. This may allow improvements in power savings, bandwidth allocation and increased QoS by accounting for human based features along with radio parameters during the resource allocation procedure in this way. It may also allow resources to be freed up and made available for use by other applications.

In some embodiments, the step of scheduling resources 204 to the user equipment in order to provide the service may comprise scheduling resources to the user equipment using a reinforcement learning agent of a second machine learning model.

The skilled person will be familiar with reinforcement learning and reinforcement learning agents, however, briefly, reinforcement learning is a type of machine learning process whereby a reinforcement learning agent (e.g. algorithm) is used to perform actions on a system to adjust the system according to an objective (which may, for example, comprise moving the system towards an optimal or preferred state of the system). The reinforcement learning agent receives rewards based on whether each action changes the system in compliance with the objective (e.g. towards the preferred state), or against the objective (e.g. further away from the preferred state). The reinforcement learning agent therefore adjusts parameters in the system with the goal of maximising the rewards received.

Put more formally, a reinforcement learning agent receives an observation from the environment in state S and selects an action to maximize the expected future reward r. Based on the expected future rewards, a value function V for each state can be calculated and an optimal policy $\pi$ that maximizes the long term value function can be derived.

In the context of this disclosure, the telecommunications network is the "environment" in the state S. The "observations" comprise the physiological parameters, other human-related and/or radio-related features. Each "action" performed by the reinforcement learning agent comprises a radio resource scheduling decision comprising a set of radio resource allocation parameters. Generally, the reinforcement learning agents herein receive feedback in the form of a reward or credit assignment every time they perform an adjustment (e.g. action). As noted above, the goal of the reinforcement learning agents herein is to maximise the reward received.

Examples of reinforcement learning agents and reinforcement learning schemes that may be used for the second machine learning model include, but are not limited to, Q learning models, Deep Deterministic Policy Gradient (DDPG), Deep Q-learning (DQN), State-Action-Reward-State-Action (SARSA).

In some embodiments, the reinforcement learning agent receives a positive reward if the scheduled resources satisfy:

$$\text{delay} <= \text{delay perception threshold} \quad [1]$$

E.g. if the delay is below the threshold that is perceivable (or predicted as being perceivable) by the user, given their cognitive state.

As noted above, generally, the larger the delay perception threshold, the larger the margin for satisfying this delay is given to the network and therefore the larger the range of power allocation or PRB action selection the network can take so as to minimize energy consumption.

In some embodiments, the reinforcement learning agent may further receive a positive reward if the scheduled resources maximise the expression:

$$a*\text{bitrate} - b*\text{energy} \quad [2]$$

wherein the parameter bitrate comprises a bitrate at which the service is provided to the user, the parameter energy comprises a measure of the energy needed by the node to provide the service to the user at the bitrate, and a and b comprise weighting values.

a and b may comprise multi-objective weights ($0<a<1$, $0<b<1$) that can be adopted for realizing a tradeoff between bitrate and energy efficiency.

In some embodiments, the reinforcement learning agent may further receive a positive reward if the scheduled resources satisfy:

$$\text{delay} <= \text{network\_delay\_threshold} \quad [3]$$

wherein the parameter network_delay_threshold comprises a parameter related to a delay permitted by the network. For example, the network_delay_threshold may be a parameter related to an underlying application requirement or machine type device requirement. For instance, as an example of a network_delay_threshold, for Ultra-reliable low-latency communication (URLLC) in 5G NR, the requirements are 99.999% success probability for transmitting a packet of 32 bytes within 1 ms. In this way, the delay requirements of the underlying application may still be accounted for.

Constraint [1] encourages the reinforcement learning agent to schedule sufficient resources to ensure that the delay is less than the delay perception threshold, thus allocating resources more efficiently. If the delay is reduced significantly below the delay perception threshold, the human user will not be able to discern the difference (compared to if it is just below the delay perception threshold). This delay perception threshold is determined by the capabilities of the human brain, based on the physiological parameters. Constraints [2] and [3] guarantee that the delay is limited by the requirement of the underlying application and that the resources provided maximise bit-rate for the minimal energy usage. Each user or machine type device can have a different application with different QoS requirements. The variables of this optimization problem could be but are not limited to parameters such as: power allocation level, resource block allocation, and beam selection.

The method 200 may then comprise allocating resources, in accordance with to the determined scheduling of resources, to the UE. In other words, providing the service to the UE with the scheduled resources.

The key difference between the proposed problem formulation and conventional RB allocation problems is seen in the QoS delay requirement where the network explicitly accounts for the human brain's delay needs. By taking into account the features of the brain of the human UEs, the network can avoid wasting resources by allocating more power to a UE, solely based on the application QoS, while ignoring how the brain of the human carrying the UE perceives this QoS. The use of physiological parameters may be particularly beneficial as these may more closely correlate with the individual user's perception capabilities and alertness, compared to other human-centric parameters, for example.

In further embodiments, the reinforcement learning agent may receive a reward based on packet loss, for example, a positive reward if the packet loss is below a threshold (e.g. required for the respective service).

A detailed embodiment wherein the second machine learning model comprises a reinforcement learning agent is provided below.

Model initialization: In this embodiment, the weights of the reinforcement learning agent may be first initialized offline based on conventional rule-based algorithms which consider radio related parameters only. For instance, for resource block allocation, one could consider round robin or proportional fairness algorithms. The machine learning model can be, for example, a random forest, convolutional neural network or feed-forward neural network.

Model training: The model is then trained to account for human-based metrics alongside the channel state information. For the training phase, we consider users under different network conditions, user activity level, and user state. The state definition, action state, and reward function of the proposed reinforcement learning technique are summarized as follows:

State: corresponds to a set of radio features and human state features:
  Physiological parameters, can be, but are not limited to:
    Heart rate
    level of activity: number of steps/sec
    stress level
    type of activity: walking, dancing, static, running, biking, . . .
    level of fatigue
  Further human-centric parameters include, for example:
    Gender
    Age
    time of the day
  Radio-related features:
    channel state information (CSI)
    RSRP/RSRQ/RSSI For instance, high heart rate can reflect certain state of the user such as stress level and high activity which is crucial for how the human brain perceives its environment and particularly a video stream application. Under such conditions, a person's brain is in a tired state and therefore the delay perception of his brain is high and the user may not be able to perceive the difference between a very good video and a good video (and hence the operator may take advantage to allocate less power/bandwidth for instance). The authors in the paper by Paweł Motyka, Martin Grund, Norman Forschack, Esra Al, Arno Villringer, and Michael Gaebler, entitled "Interactions between cardiac activity and conscious somatosensory perception" investigate the link between perceptual awareness and cardiac signals. They show that the physiological state of the body influences how we perceive the world. Also note that the stress level, level of fatigue, and type of activity also have a strong correlation with heart rate (higher heart rate under stress or intense physical activity) which therefore impact one's perceptual awareness and video quality assessment under different conditions.

The authors in the paper by Milan Mirkovic, Petar Vrgovic, Dubravko Culibrk, Darko Stefanovic, and Andras Anderla, entitled "Evaluating the Role of Content in Subjective Video Quality Assessment" analyze differences between human cognitive, affective, and conative responses to a set of videos commonly used for video quality assessment and a set of videos specifically chosen to include video content which might affect the judgment of evaluators when perceived video quality is in question. They show that cognitive mental activities are mostly observed as a "rational," or "objective" peace of mind. These activities are thought to be responsible for processing information that people get from their sensory systems via attention and memory. Moreover, it is highlighted in this paper that other factors pertinent to different populations (gender-wise, culture-wise, and demographically wise) that impact subjective perception of video quality may thus be taken into account when video quality assessment tasks are in question.

As such, the above highlighted human-related features are important for resource allocation problem in wireless networks where an operator can account for the quality of experience or the human perception of the service and adjust the radio resources accordingly resulting in an energy efficient management of the network.

Action: a set of radio resource allocation parameters. Depending on the underlying application at the user side, one could consider adjusting one or more of the following radio related parameters. Examples can be but are not limited to:
  Transmission power level
  Number of allocated resource blocks
  Beam selection Reward: The multi-objective weighted function defined in the above optimization problem which accounts for:
  Rate
  Latency
  Energy efficiency The reinforcement learning agent may be rewarded based on the following scheme:

$$\text{Minimize} - a*\text{Bitrate} + b*\text{Energy} \quad [a]$$

$$\text{Subject to: delay} <= \text{delay perception threshold} \quad [b]$$

$$\text{delay} <= \text{Machine type device requirements} \quad [c]$$

The delay perception threshold in (3) can be deduced from the user rating results of the supervised learning scheme described above with respect to the first machine learning model.

Real operation: In practice, the node 100 can collect physiological parameters, and/or other human-related data whenever a given user registers in the network or by using the sensors of a user's mobile device. This may be subject e.g. to the user's consent to this data being collected for use in this manner, and/or local personal data usage laws.

If the physiological parameters (and/or other human-related features) are not available, then the radio resources may be allocated based on the radio-related features only, as done in conventional wireless networks. E.g. the node 100 may revert to a legacy scheduling procedure.

The reinforcement learning agent (e.g. second model) may be continuously trained online based on user input that can be fed to the network (human-in-the-loop). For example, the network may request feedback from the user on their corresponding quality of experience, such as, for example, a metric that assesses the delay perceived by the user. Safe exploration techniques can be adopted for guaranteeing the QoS for the end users when randomly selecting an action. The skilled person will be familiar with safe methods of exploration using a reinforcement learning agent in a communications network. For example, studies of network conditions which allow safe exploration include the paper by T. Mannuci, E. Kampen, C. Visser, and Q. Cu, entitled "*Safe Exploration Algorithms for Reinforcement Learning Controllers*", IEEE Transactions on Neural Networks and Learning Systems, vol. 29, no. 4, April 2018.

Figure 3:
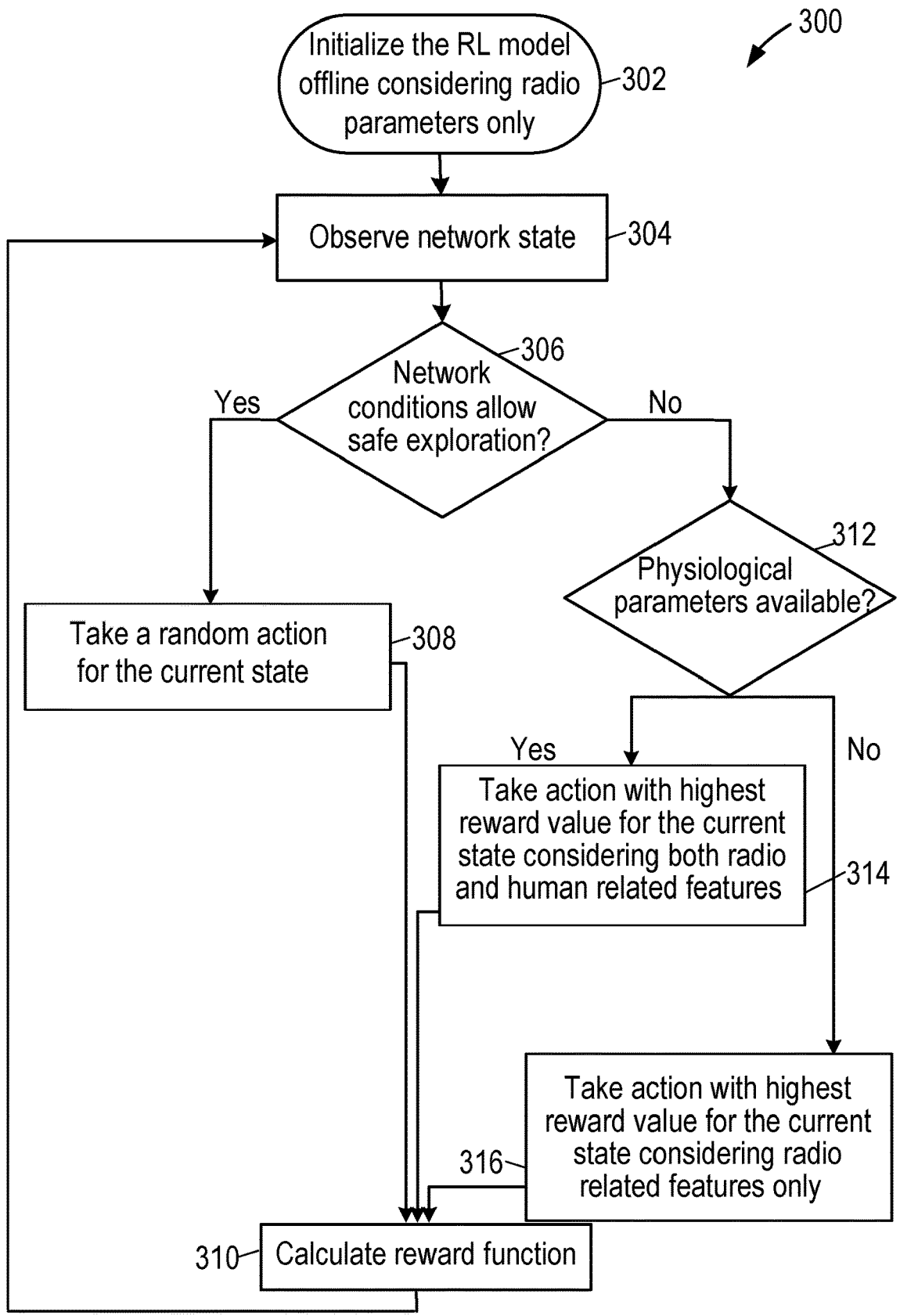
FIG. 3 illustrates a method in a node of a communications network according to some embodiments.

Turning now to FIG. 3, which illustrates an embodiment for resource allocation. In the embodiment of FIG. 3, a method may comprise initialising 302 the reinforcement learning procedure offline, using radio parameters only. The network state may then be observed 304. If the network conditions allow safe exploration, then a random action (e.g. "exploratory action") may be taken for the current state. The action may comprise an exploratory action with respect to power level, beam selection, physical resource block (PRB) allocation etc. A reward may then be allocated for the action in 310. If the network conditions do not allow safe exploration in block 306, then in block 312 it is determined whether physiological parameters of the user are available. If they are, then the method comprises taking an action known to have the highest reward value for the current state, considering both radio and human related features. The action may comprise selection of a power level, beam selection, or PRB allocation as in block 308. If in block 312, no physiological parameters are available, then the method may comprise taking 316 the action with the highest reward value for the current state considering radio related features only. Again, the action may comprise selecting a power level, beam selection, and/or PRB allocation. After either step 314 or 316, the method comprises allocating 310 a reward based on the reward function. The method then moves back to step 304, in preparation for taking the next action.

In this way, an exploration/exploitation strategy for the second machine learning model may be devised that takes the availability of physiological parameters into account when determining an appropriate action. This allows for safe exploration for online model updates.

In another embodiment, there is provided a computer program product comprising a computer readable medium, the computer readable medium having computer readable code embodied therein, the computer readable code being configured such that, on execution by a suitable computer or processor, the computer or processor is caused to perform the method or methods described herein.

Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer implemented method of operating a node of a communications network for scheduling radio resources to a user equipment, UE, ("UE") in order to provide a service to a user of the UE, the method comprising:
   obtaining one or more physiological parameters of the user of the UE; and
   scheduling resources to the UE, based on the one or more physiological parameters, so as to provide the service to the UE with a predetermined quality of experience that is associated with whether the user perceives a delay in the service,
   wherein scheduling the resources to the UE comprises:
   determining from the one or more physiological parameters a delay perception threshold at which the delay is perceptible to the user; and
   scheduling the resources to the UE based on the delay perception threshold.

2. The computer implemented method of claim 1, wherein scheduling the resources to the UE based on the delay perception threshold comprises scheduling the resources so as to provide the service with the delay that is less than the delay perception threshold.

3. The computer implemented method of claim 1, wherein determining from the one or more physiological parameters the delay perception threshold comprises:
   predicting the delay perception threshold using a first machine learning model that takes as input the one or more physiological parameters and outputs a prediction of the delay perception threshold of the user, based on the one or more physiological parameters.

4. The computer implemented method of claim 3, wherein the first machine learning model was trained using training data comprising including training examples, each training example including a set of example values of the one or more physiological parameters for an example user and a ground truth delay perception threshold for the example user, at the time the example values of the one or more physiological parameters were obtained.

5. The computer implemented method of claim 4, wherein the ground truth delay perception threshold is based on feedback provided by the example user, of a quality of experience of an example service provided to the example user.

6. The computer implemented method of claim 1, wherein scheduling the resources to the UE based on the delay perception threshold comprises:
   providing the service using fewer resources if the delay perception threshold of the user is higher compared to if the delay perception threshold of the user is lower.

7. The computer implemented method of claim 6, wherein providing the service using the fewer resources comprises:
   transmitting packets related to the service with lower power; and/or
   allocating fewer resource blocks to the service.

8. The computer implemented method of claim 1, wherein scheduling the resources to the user equipment in order to provide the service comprises:
   scheduling the resources to the user equipment using a reinforcement learning agent of a second machine learning model.

9. The computer implemented method of claim 8, wherein the predetermined quality of experience is based on whether the user perceives the delay in the service,
   wherein scheduling the resources to the UE comprises:
   determining from the one or more physiological parameters the delay perception threshold at which the delay is perceptible to the user; and
   scheduling the resources to the UE based on the delay perception threshold, and wherein the reinforcement learning agent receives a positive reward if the scheduled resources satisfy:
   delay=<delay perception threshold.

10. The computer implemented method of claim 8, wherein the reinforcement learning agent receives a positive reward if the scheduled resources maximize the expression: $a*bitrate - b*energy$, and wherein the parameter bitrate comprises a bitrate at which the service is provided to the user, the parameter energy comprises a measure of the energy needed by the node to provide the service to the user at the bitrate, and a and b comprise weighting values.

11. The computer implemented method of claim 8, wherein the reinforcement learning agent receives a positive reward if the scheduled resources satisfy:
   delay<=network_delay_threshold, and wherein the parameter network_delay_threshold comprises a parameter related to a delay permitted by the network.

12. The computer implemented method of claim 1, wherein obtaining the one or more physiological parameters of the user of the UE comprises obtaining the one or more physiological parameters from one or more sensors on the UE.

13. The computer implemented method of claim 1, wherein the service comprises a virtual reality application or gaming application.

14. The computer implemented method of claim 1, wherein the one or more physiological parameters comprise one or more of the following:
   a heart rate;
   a blood pressure;
   a measure of stress; and
   a measure of an activity level of the user.

15. The computer implemented method of claim 1, further comprising:
   allocating the resources in accordance with the determined scheduling of the resources to the UE.

16. A node in a communications network for scheduling radio resources to a user equipment, UE, ("UE") in order to provide a service to a user of the UE, the node comprising:
   processing circuitry; and
   memory coupled to the processing circuitry and having instructions stored therein that are executable by the processing circuitry to cause the node to perform operations comprising:
   obtaining one or more physiological parameters of the user of the UE; and
   scheduling resources to the UE, based on the one or more physiological parameters, so as to provide the service to the UE with a predetermined quality of experience that is associated with whether the user perceives a delay in the service,
   wherein scheduling the resources to the UE comprises:
   determining from the one or more physiological parameters a delay perception threshold at which the delay is perceptible to the user; and
   scheduling the resources to the UE based on the delay perception threshold.

17. The node of claim 16, wherein scheduling the resources to the UE based on the delay perception threshold comprises scheduling the resources so as to provide the service with the delay that is less than the delay perception threshold.

18. The node of claim 16, wherein determining from the one or more physiological parameters the delay perception threshold comprises:
   predicting the delay perception threshold using a first machine learning model that takes as input the one or more physiological parameters and outputs a prediction of the delay perception threshold of the user, based on the one or more physiological parameters.

19. The node of claim 16, wherein the first machine learning model was trained using training data including training examples, each training example including a set of example values of the one or more physiological parameters for an example user and a ground truth delay perception threshold for the example user, at the time the example values of the one or more physiological parameters were obtained, and wherein the ground truth delay perception threshold is based on feedback provided by the example user, of a quality of experience of an example service provided to the example user.

20. A non-transitory computer-readable medium having instructions stored therein that are executable by processing circuitry of a node in a communications network to cause the node to perform operations for scheduling radio resources to a user equipment ("UE") in order to provide a service to a user of the UE, the operations comprising:
   obtaining one or more physiological parameters of the user of the UE; and
   scheduling resources to the UE, based on the one or more physiological parameters, so as to provide the service to the UE with a predetermined quality of experience that is associated with whether the user perceives a delay in the service, wherein scheduling the resources to the UE comprises:
   determining from the one or more physiological parameters a delay perception threshold at which the delay is perceptible to the user; and
   scheduling the resources to the UE based on the delay perception threshold.

* * * * *